US011984196B2

(12) United States Patent
Byrnes et al.

(10) Patent No.: US 11,984,196 B2
(45) Date of Patent: May 14, 2024

(54) COMMUNITY ASSIGNMENTS IN IDENTITY BY DESCENT NETWORKS AND GENETIC VARIANT ORIGINATION

(71) Applicant: Ancestry.com DNA, LLC, Lehi, UT (US)

(72) Inventors: Jake Kelly Byrnes, San Francisco, CA (US); Julie M. Granka, San Francisco, CA (US); Shannon Hateley, San Francisco, CA (US); Ladan Doroud, Millbrae, CA (US)

(73) Assignee: ANCESTRY.COM DNA, LLC, Lehi, UT (US)

( * ) Notice: Subject to any disclaimer, the term of this patent is extended or adjusted under 35 U.S.C. 154(b) by 259 days.

(21) Appl. No.: 17/531,438

(22) Filed: Nov. 19, 2021

(65) Prior Publication Data

US 2022/0076782 A1   Mar. 10, 2022

Related U.S. Application Data

(62) Division of application No. 17/044,223, filed as application No. PCT/IB2019/052788 on Apr. 4, 2019, now Pat. No. 11,238,957.

(60) Provisional application No. 62/653,416, filed on Apr. 5, 2018, provisional application No. 62/653,420, filed on Apr. 5, 2018.

(51) Int. Cl.
| | |
|---|---|
| *G01N 33/48* | (2006.01) |
| *G06N 20/00* | (2019.01) |
| *G16B 20/20* | (2019.01) |
| *G16B 20/40* | (2019.01) |
| *G16B 30/10* | (2019.01) |
| *G16B 40/00* | (2019.01) |

(52) U.S. Cl.
CPC ............ *G16B 20/20* (2019.02); *G06N 20/00* (2019.01); *G16B 20/40* (2019.02); *G16B 30/10* (2019.02); *G16B 40/00* (2019.02)

(58) Field of Classification Search
None
See application file for complete search history.

(56) References Cited

U.S. PATENT DOCUMENTS

| | | | |
|---|---|---|---|
| 4,201,386 A | 5/1980 | Seale et al. | |
| 5,115,504 A | 5/1992 | Belove et al. | |
| 5,246,374 A | 9/1993 | Boodram | |
| 5,413,908 A | 5/1995 | Jeffreys | |
| 5,467,471 A | 11/1995 | Bader | |
| 5,978,811 A | 11/1999 | Smiley | |
| 6,049,803 A | 4/2000 | Szalwinski | |
| 6,105,147 A | 8/2000 | Molloy | |
| 6,277,567 B1 | 8/2001 | Graziosi | |
| 6,528,260 B1 | 3/2003 | Blumenfeld et al. | |
| 6,570,567 B1 | 5/2003 | Eaton | |
| 6,886,015 B2 | 4/2005 | Notargiacomo et al. | |
| 6,950,753 B1 | 9/2005 | Rzhetsky et al. | |
| 7,957,907 B2 | 6/2011 | Sorenson et al. | |
| 8,185,557 B2 | 5/2012 | Slinker | |
| 8,224,821 B2 | 7/2012 | Graham et al. | |
| 8,510,057 B1 | 8/2013 | Avey et al. | |
| 8,738,297 B2 | 5/2014 | Sorenson et al. | |
| 8,855,935 B2 | 10/2014 | Myres et al. | |
| 9,116,882 B1 | 8/2015 | Macpherson et al. | |
| 9,213,947 B1 | 12/2015 | Do et al. | |
| 9,367,800 B1 | 6/2016 | Do et al. | |
| 9,836,576 B1 | 12/2017 | Do et al. | |
| 9,940,433 B2 | 4/2018 | Han et al. | |
| 10,025,877 B2 | 7/2018 | Macpherson | |
| 10,223,498 B2 | 3/2019 | Han et al. | |
| 2002/0143578 A1 | 10/2002 | Cole et al. | |
| 2003/0032015 A1 | 2/2003 | Toivonen et al. | |
| 2003/0113727 A1 | 6/2003 | Girn et al. | |
| 2003/0113756 A1 | 6/2003 | Mertz | |

(Continued)

FOREIGN PATENT DOCUMENTS

| | | |
|---|---|---|
| WO | WO 2008/042232 A2 | 4/2008 |
| WO | WO 2016/073953 A1 | 5/2016 |
| WO | WO 2016/193891 A1 | 12/2016 |

OTHER PUBLICATIONS

Alexander, D.H. et al., "Enhancements to the Admixture Algorithm for Individual Ancestry Estimation," BMC Bioinformatics 12(1), 246, Jun. 18, 2011, pp. 1-6.
Alexander, D.H., et al., "Fast model-based estimation of ancestry in unrelated individuals," Genome research, Sep. 2009, vol. 19, No. 9, pp. 1655-1664.
Atzmon, G. et al., "Abraham's Children in the Genome Era: Major Jewish Diaspora Populations Comprise Distinct Genetic Clusters with Shared Middle Eastern Ancestry," American Journal of Human Genetics 86(6), Jun. 11, 2010, pp. 850-859.
Belkin, M. et al., "Laplacian Eigenmaps for Dimensionality Reduction and Data Representation," Neural Computation 15, Jun. 2003, pp. 1373-1396.

(Continued)

*Primary Examiner* — Anna Skibinsky
(74) *Attorney, Agent, or Firm* — Fenwick & West LLP

(57) ABSTRACT

Disclosed are techniques for characterizing variants of interest and predicting assignments of individuals to communities based on obtained genetic information. To characterize a variant, DNA datasets of reference individuals are accessed and used to generate a cluster with additional individuals. Reference individuals carry a variant at a genetic locus and the additional individuals share IBD with reference individuals. Statistics of genealogical data of the cluster are generated. A result summarizing the characterization of the variant is generated based on the statistics. To determine if an individual belongs to a community, a subset of the individual's haplotypes are inputted into a community-specific model. The model is trained using the training samples that each include haplotypes of reference individuals and a label identifying whether the reference individual belongs to the community. Based on the output of the model, it is determined whether the individual is a member of the community.

20 Claims, 9 Drawing Sheets

(56) References Cited

U.S. PATENT DOCUMENTS

| | | |
|---|---|---|
| 2003/0172065 A1 | 9/2003 | Sorenson et al. |
| 2003/0195707 A1 | 10/2003 | Schork et al. |
| 2003/0204418 A1 | 10/2003 | Ledley |
| 2004/0122705 A1 | 6/2004 | Sabol et al. |
| 2004/0229231 A1 | 11/2004 | Frudakis et al. |
| 2004/0243531 A1 | 12/2004 | Dean |
| 2005/0147947 A1 | 7/2005 | Cookson et al. |
| 2005/0149522 A1 | 7/2005 | Cookson et al. |
| 2006/0020398 A1 | 1/2006 | Vernon et al. |
| 2006/0136143 A1 | 6/2006 | Avinash et al. |
| 2006/0161535 A1 | 7/2006 | Holbrook |
| 2007/0037182 A1 | 2/2007 | Gaskin et al. |
| 2008/0027656 A1 | 1/2008 | Parida |
| 2008/0154566 A1 | 6/2008 | Myres et al. |
| 2008/0228751 A1 | 9/2008 | Kenedy et al. |
| 2008/0255768 A1 | 10/2008 | Martin et al. |
| 2009/0100030 A1 | 4/2009 | Isakson et al. |
| 2009/0299645 A1 | 12/2009 | Colby et al. |
| 2010/0218228 A1 | 8/2010 | Walter |
| 2011/0093448 A1 | 4/2011 | Rafi et al. |
| 2011/0161168 A1 | 6/2011 | Dubnicki |
| 2012/0218289 A1 | 8/2012 | Rasmussen et al. |
| 2013/0085728 A1 | 4/2013 | Tang et al. |
| 2013/0149707 A1 | 6/2013 | Sorenson et al. |
| 2014/0067355 A1 | 3/2014 | Noto et al. |
| 2014/0108527 A1 | 4/2014 | Aravanis et al. |
| 2014/0278138 A1 | 9/2014 | Barber et al. |
| 2015/0100243 A1 | 4/2015 | Myres et al. |
| 2016/0350479 A1* | 12/2016 | Han ................. G16C 20/60 |
| 2017/0011042 A1 | 1/2017 | Kermany et al. |
| 2017/0262577 A1* | 9/2017 | Ball ................. G16B 40/20 |
| 2017/0277827 A1 | 9/2017 | Granka et al. |
| 2017/0329891 A1 | 11/2017 | Macpherson et al. |
| 2019/0034587 A1 | 1/2019 | Anderson et al. |
| 2019/0147973 A1 | 5/2019 | Han et al. |

OTHER PUBLICATIONS

Bengio, Y. et al., "Out-of-Sample Extensions for LLE, Isomap, MOS, Eigenmaps and Spectral Clustering," NIPS'03: Proceedings of the 16th International Conference on Neural Information Processing Systems, Dec. 2003, pp. 177-184.

Blondel, V.D. et al., "Fast Unfolding of Community Hierarchies in Large Networks," Journal of Statistical Mechanics: Theory and Experiment, Oct. 9, 2008, p. 1-12.

Browning, B.L. et al., "Efficient Multilocus Association Testing for Whole Genome Association Studies Using Localized Haplotype Clustering," Genetic Epidemiology, 2007, Vo. 31, pp. 365-375.

Browning, S.R. et al., "High-resolution detection of Identity by Descent in unrelated individuals," The American Journal of Human Genetics, vol. 86, Apr. 9, 2010, pp. 526-539.

Browning, S.R. et al., "Rapid and Accurate Haplotype Phasing and Missing-Data Inference for Whole-Genome Association Studies by Use of Localized Haplotype Clustering," The American Journal of Human Genetics, Nov. 2007, pp. 1084-1096, vol. 81.

Browning, S.R., "Multilocus Association Mapping Using Variable-Length Markov Chains," The American Journal of Human Genetics, Jun. 2006, vol. 78, pp. 903-913.

Butler, John M., "Commonly Used Short Tandem Repeat Markers," Forensic DNA Typing, Chapter 5, 2001, pp. 53-54, Academic Press.

Cann, H.M. et al., "A human genome diversity cell line panel," Science, Apr. 2002, vol. 296, No. 5566, pp. 261-262.

Capoccia, A., et al. "Detecting communities in large networks," Physica A, vol. 352, Jan. 25, 2005, pp. 669-676.

Carmi, S. et al., "Sequencing an Ashkenazi Reference Panel Supports Population-Targeted Personal Genomics and Illuminates Jewish and European Origins," Nature Communications 5:4835, Sep. 9, 2014, pp. 1-9.

Carmi, S. et al., "The Variance of Identity-by-Descent Sharing in the Wright-Fsher Model," Genetics 193(3), Mar. 2013, pp. 911-928.

Cavalli-Sforza, L.L. "The human genome diversity project: past, present and future," Nature Reviews Genetics, Apr. 2005, vol. 6, No. 4. pp. 333-340.

Coifman, R.R. et al., "Diffusion Maps," Applied and Computational Harmonic Analysis, vol. 21, Jun. 19, 2006, pp. 5-30.

Corach et al., "Mass disasters: Rapid molecular screening of human remains by means of short tandem repeats typing," Electrophoresis (1995) vol. 16, pp. 1617-1623.

Curtis, R.E. et al., "Estimation of recent ancestral origins of individuals on a large scale," KDD '17, Aug. 2017, pp. 1417-1425.

Dermitzakis, E. et al., "The International HapMap 3 Consortium. Integrating common and rare genetic variation in diverse human populations," Nature, 2010, vol. 467, 8 pages.

Durand, E.Y. et al., "Reducing Pervasive False-Positive Identical-by-Descent Segments Detected by Large-Scale Pedigree Analysis," Molecular Biology and Evolution 31(8), Apr. 30, 2014, pp. 2212-2222.

European Patent Office, Extended European Search Report and Opinion, EP Patent Application No. 1978216.6, dated Nov. 12, 2021, nine pages.

Falush, D. et al., "Inference of Population Structure Using Multilocus Genotype Data: Linked Loci and Correlated Allele Frequencies," Genetics Society of America, 2003, vol. 164, pp. 1567-1587.

Fortunato, S. et al., "Resolution Limit in Community Detection," Proceedings of the National Academy of Sciences 104(1), Jan. 2, 2007, pp. 36-41.

Fortunato, S., "Community Detection in Graphs," Physics Reports 486, Dec. 4, 2009, pp. 75-174.

Francioli, L. et al., Whole-Genome Sequence Variation, Population Structure and Demographic History of the Dutch Population, Nature Genetics 46(8), Aug. 2014, pp. 818-825.

Gauvin, H. et al., "Genome-Wide Patterns of Identity-by-Descent Sharing in the French Canadian Founder Population," European Journal of Human Genetics 22, Oct. 16, 2013, pp. 814-821.

Genealogy Blog With Attitude, "Surnames, 23andMe, and AncestryDNA: Making the Most of Match Counts and "Enrichment"—Genealogy and Genomics," Apr. 4, 2015, 24 pages, [Online] Retrieved Jan. 23, 2019, Retrieved from the Internet: <URL: http://web.archive.org/web/20150404210843/http:I/ourpuzzlingpast.com/gene- blog/2015/01/25/surnames-23andme-and-ancestrydnamaking-the-most-of-match-c- ounts-and-enrichment>.

Genealogy definition, Merriam-Webster Online Dictionary, 2004, http://www.mw.com/cqibin/dictionary?book=Dictionary&va=genealogy (1 page).

Girvan, M. et al., "Community Structure in Social and Biological Networks," PNAS 99(12), Jun. 11, 2002, pp. 7821-7826.

Good, B.H. et al., "Performance of Modularity Maximization in Practical Contexts," Physical Review E 81(4), Apr. 15, 2010, pp. 1-19.

Gusev, A. et al., "Whole Population, Genome-Wide Mapping of Hidden Relatedness," Genome Research, 2009, pp. 318-326, vol. 19.

Han, L. et al., "Identity by descent estimation with dense genome-wide genotype data," Genet Epidemiol., vol. 35, No. 6, Sep. 2011, pp. 557-567.

Hao, W. et al., "Probabilistic Models of Genetic Variation in Structured Populations Applied to Global Human Studies," arXiv:1312.2041, Dec. 7, 2013, pp. 1-35.

International Hapmap Consortium, "A haplotype map of the human genome," Nature, Oct. 2005, vol. 437, No. 27, pp. 1299-1320.

International Hapmap Consortium, "A second generation human haplotype map of over 3.1 million SNPs," Nature, Oct. 2007, vol. 449, No. 7164, pp. 1-30.

Jarvis, J.P. et al., "Patterns of Ancestry, Signatures of Natural Selection, and Genetic Association with Stature in Western African Pygmies," PLoS Genetics, 2012, vol. 8, No. 4, pp. 1-15.

King, T et al., "What's in a Name? Y Chromosomes, Surnames and the Genetic Genealogy Revolution," Trends in Genetics, 2009, pp. 351-360, vol. 25, No. 8.

Lee, A.B. et al., "A Spectral Graph Approach to Discovering Genetic Ancestry," Annals of Applied Statistics 4(1), Mar. 2010, pp. 179-202.

(56) References Cited

OTHER PUBLICATIONS

Lee, A.B. et al., "Discovering Genetic Ancestry Using Spectral Graph Theory," Genetic Epidemiology 34, May 19, 2009, pp. 51-59.
McGraw, P.N. et al., "Laplacian Spectra as a Diagnostic Tool for Network Structure and Dynamics," Physical Review E 77(3), Mar. 4, 2008, pp. 1-14.
McVean, G., "A Genealogical Interpretation of Principal Components Analysis," PLoS Genetics 5(10), Oct. 16, 2009, pp. 1-10.
Meirmans, P.G., "The Trouble with Isolation by Distance," Molecular Ecology 21(12), May 11, 2012, pp. 2839-2846.
Morrison, AC et al., "Prediction of Coronary Heart Disease Risk using a Genetic Risk Score: The Atherosclerosis Risk in Communities Study," American Journal of Epidemiology, 2007, vol. 166, No. 1, pp. 28-35.
Newman, M.E.J., "Communities, Modules and Large-Scale Structure in Networks," Nature Physics 8(1), Jan. 2012, pp. 25-31.
Noto, K. et al., "Underdog: A Fully-Supervised Phasing Algorithm That Learns from Hundreds of Thousands of Samples and Phases in Minutes," Oct. 20, 2014, 1 page.
Novembre, J. et al., "Genes Mirror Geography within Europe," Nature 456(7218), Nov. 2008, pp. 98-101.
Palamara, P.F. et al., "Inference of Historical Migration Rates via Haplotype Sharing," Bioinformatics 29(13), Jul. 2013, pp. 180-188.
Palamara, P.F. et al., "Length Distributions of Identity by Descent Reveal Fine-Scale Demographic History," American Journal of Human Genetics 91(5), Nov. 2, 2012, pp. 809-822.
Palin, K. et al., "Identity-by-Descent-Based Phasing and Imputation in Founder Populations Using Graphical Models," Genetic Epidemiology, vol. 35, Oct. 17, 2011, pp. 853-860.
Patterson, N. et al., "Population structure and eigenanalysis," PLoS genetics, Dec. 2006, vol. 2, No. 12, pp. 2074-2093.
PCT International Search Report and Written Opinion, International Application No. PCT/IB2019/052788, dated Aug. 9, 2019, 10 pages.
PCT International Search Report and Written Opinion, PCT Application No. PCT/IB2016/053166, dated Sep. 6, 2016, 13 pages.
Platt, J.C. et al., "Probabilistic Outputs for Support Vector Machines and Comparisons to Regularized Likelihood Methods," Microsoft Research, Mar. 26, 1999, pp. 1-11.
Price, AL. et al., "Sensitive Detection of Chromosomal Segments of Distinct Ancestry in Admixed Populations," PLoS Genetics, 2009, vol. 5, No. 6, pp. 1-18.
Pritchard, J.K. et al., "Inference of population structure using multilocus genotype data," Genetics Society of America, Jun. 2000, vol. 155, No. 2, pp. 945-959.
Purcell, S. et al., "PLINK: A tool set for whole-genome association and population-based linkage analyses," The American Journal of Human Genetics, vol. 81, Sep. 2007, pp. 559-575.
Purcell, S., "Plink (1.07) Documentation," May 10, 2010, 293 pages, http://pnga.mgh.harvard.edu/purcell/plink/.
Qian, Y. et al., "Efficient clustering of identity-by-descent between multiple individuals," Bioinformatics, vol. 30, No. 7, Dec. 19, 2013, pp. 915-922.
Rabiner, L.R. et al., "A Tutorial on hidden Markov Models and Selected Application in Speech Recognition," Proceedings of the IEEE, Feb. 1989, vol. 77, No. 2, pp. 257-286.
Raj, A. et al., "FastStructure: Variational Inference of Population Structure in Large SNP Data Sets," Genetics 197(2), Jun. 2014, pp. 573-589.
Ron, D. et al., "On the Learnability and Usage of Acyclic Probabilistic Finite Automata," Journal of Computer and System Sciences, vol. 56, 1998, pp. 133-152.
Scheet, P. et al., "A Fast and Flexible Statistical Model for Large-Scale Population Genotype Data: Applications to Inferring Missing Genotypes and Haplotypic Phase," The American journal of Human Genetics, Apr. 2006, vol. 78, pp. 629-644.
Seligsohn, U. et al., "Genetic Susceptibility to Venous Thrombosis," The New England Journal of Medicine, Apr. 19, 2001, vol. 344, No. 16, pp. 1222-1231.
Staples, J. et al., "PRIMUS: Rapid Reconstruction of Pedigrees from Genome-wide Estimates of Identity by Descent, " The American Journal of Human Genetics, vol. 95, Nov. 6, 2014, pp. 553-564.
Stedman's Medical Dictionary 27th Edition, 2000, p. 703.
Stevens, E. L., et al., "Inference of Relationships in Population Data Using Identity-by-Descent," PLOS Genetics, vol. 7, Iss. 9, Sep. 22, 2011, pp. 1-15.
Sundquist, A et al., "Effect of genetic divergence in identifying ancestral origin using HAPPA," Genome Research, 2008, Vo. 18, 8 pages.
The 1000 Genomes Project Consortium, "An Integrated Map of Genetic Variation from 1,092 Human Genomes," Nature 491, Nov. 2012, pp. 56-65.
Tipping, M.E., "Sparse Bayesian Learning and the Relevance Vector Machine," Journal of Machine Learning Research, 2001, vol. 1, pp. 211-244.
Von Luxburg, U., "A Tutorial on Spectral Clustering," Statistics and Computing 17(4), Aug. 22, 2007, pp. 395-416.
Website printout, Family Tree DNA, http://www.familytreedna.com/main.html, Feb. 8, 2001 (2 pages).
Website printout, Oxford Ancestors, http://www.oxfordancestors.com, Feb. 12, 2001 (4 pages).
Weedon, M.N. et al., "Combining Information from Common Type 2 Diabetes Risk Polymorphisms Improves Disease Prediction," PLoS Medicine, Oct. 2006, vol. 3, No. 10, pp. 1877-1882.
Welch, B.L., "The Generalization of "Student's" Problem when Several Different Population Variances are Involved," Biometrika 34(1-2), 1947, pp. 28-35.
Wikipedia, "Identity by descent," Feb. 13, 2015, 5 pages, [Online] Retrieved Jan. 23, 2019, Retrieved from the Internet: <URL: https://en.wikipedia.org/w/index.php?title=identity_by_descent&oldid=6468-73616.>.
Williams, A.L. et al., "Phasing of Many Thousands of Genotyped Samples," The American Journal of Human Genetics, Aug. 10, 2012, vol. 91, pp. 238-251.
Wilson et al., "Genealogical Inference from Microsatellite Data," Genetics (1998) 150:499-510.
Yang, Q. et al., "Improving the Prediction of Complex Diseases by Testing for Multiple Disease-Susceptibility Genes," American Journal of Human Genetics, 2003, vol. 72, pp. 636-649.
Yoon, B.J., "Hidden Markov Models and their Applications in Biological Sequence Analysis," Current Genomics, 2009, vol. 10, pp. 402-415.
Zelnik-Manor, L. et al., "Self-Tuning Spectral Clustering," In Advances in Neural Information Processing Systems 17, Jan. 2004, pp. 1601-1608.
Zhang, J., "Ancestral Informative Marker Selection and Population Structure Visualization Using Sparse Laplacian Eigenfunctions, " PLoS One 5(11), Nov. 4, 2010, pp. 1-12.
Zhao, F. et al., "Spectral Clustering with Eigenvector Selection Based on Entropy Ranking," Neurocomputing 73(10-12), Mar. 12, 2010, pp. 1704-1717.

* cited by examiner

600

900

Receive a request to generate a report of a target set of one or more variants of a user 905

Identify a group of one or more carriers that are known to be carrying the one or more variants in the specified target set 910

Access DNA datasets of the carriers 915

Access DNA datasets of additional individuals who share IBD with at least one of the carriers at a genetic locus that includes the one or more variants specified in the target set 920

Access genealogical data of the carriers and the additional individuals 925

Generate a result summarizing a characterization of the one or more variants based on an association between the one or more variants and the genealogical data of the carriers and the additional individuals 930

FIG. 9

COMMUNITY ASSIGNMENTS IN IDENTITY BY DESCENT NETWORKS AND GENETIC VARIANT ORIGINATION

CROSS-REFERENCE TO RELATED APPLICATIONS

The present application is a divisional of U.S. application Ser. No. 17/044,223, filed on Apr. 4, 2019, which is a national stage entry of International Application No. PCT/IB2019/052788, filed on Apr. 4, 2019, which claims the benefit of U.S. Provisional Patent Application No. 62/653,416 filed on Apr. 5, 2018, and U.S. Provisional Patent Application No. 62/653,420 filed on Apr. 5, 2018, which are hereby incorporated by reference in their entirety for all purposes.

BACKGROUND

The disclosed embodiments relate to assessing populations in which a variant of interest may have arisen and propagated and discovering historical populations from the pattern of genetic relationships between people.

Although humans are, genetically speaking, almost entirely identical, small differences in human DNA are responsible for some observed variation between individuals. In fact, by comparing these small differences in DNA of individuals, it is possible to detect long chromosome segments suggestive of inheritance from a recent common ancestor, and then use these detected segments to estimate how closely two people are related. The process of identifying segments suggestive of recent common inheritance is known in population genetics literature as an analysis of identity-by-descent (IBD). IBD analysis can be used to predict the familial relationship between any two people (e.g., second cousins) in a population. Learning about population structure from genetic polymorphism data is an important topic in genetics. The most widely used methods in this area are based on modeling variation in allele frequencies. These methods have shed light, for example, on historical patterns of migration in human populations. To take one example of this, prior genetic studies of the United States (US) have helped to elucidate the diversity of recent immigrants in relation to other parts of the world (e.g. Europe, Africa).

SUMMARY

Disclosed herein are techniques for characterizing variants of interest. Characterizations can provide insights into the origins, migration patterns, and historical and contemporary geographic locations of populations carrying any variant of interest. Since many variants are associated with a phenotype (e.g., a trait, a disease, or another observable characteristic), learning about a variant's origin and distribution can provide insight into the etiology of the associated phenotype and can be extended to targeting at-risk populations.

In one embodiment, a method for characterizing a variant of interest includes obtaining a DNA dataset from an individual. Genotypes of the individual are determined based on the DNA dataset. A set of reference DNA datasets is accessed. Each reference DNA dataset is associated with a reference individual, and each reference individual is a carrier of a variant at a genetic locus. In some embodiments, a phenotype or haplotype may also be chosen. A cluster includes reference individuals and additional individuals who share Identity-by-Descent (IBD) with the reference individuals is generated. The cluster may be generated based on an IBD affinity between the reference individuals and the additional individuals. In some embodiments, the cluster includes nodes, which represent individuals, and weighted edges, which represent the IBD affinity between individuals. To characterize the variant, the identified cluster is annotated with genealogical data (e.g., birth locations, surnames, ancestral birth locations, residences) based on information about the individuals in the cluster. Statistics of the genealogical data are generated to characterize the variant. Results summarizing the characterization of the variant are generated. If it is determined that the individual shares IBD with the cluster at the genetic locus, a report summarizing the characterization of the variant is provided for display.

In various embodiments, the techniques disclosed herein may additionally be used for predicting assignments of individuals to communities based on obtained genetic information. A DNA dataset is obtained for an individual. Genotypes of the individual are determined based on the DNA dataset. The genotypes are phased to generate haplotypes of the individual, and a subset of haplotypes of the individual are selected. A subset is chosen based on the features of a community of interest. The subset of the haplotypes is inputted into a community-specific model to determine whether the individual is a member of the community. The model is trained using training samples, where each training sample includes a group of haplotypes of a reference individual and a label identifying whether the reference individual belongs to the community. The reference individuals who belong to the community have one or more groups of haplotypes that are representative of the community. Haplotypes that are representative of the community may be identified by performing an enrichment analysis on haplotypes that are common among individual who are known members of the community. Based on the output of the model, it is determined whether the individual is a member of the community.

BRIEF DESCRIPTION OF THE DRAWINGS

FIG. 9 is a flow chart illustrating an additional method of characterizing a variant, according to one embodiment.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Figure 1:
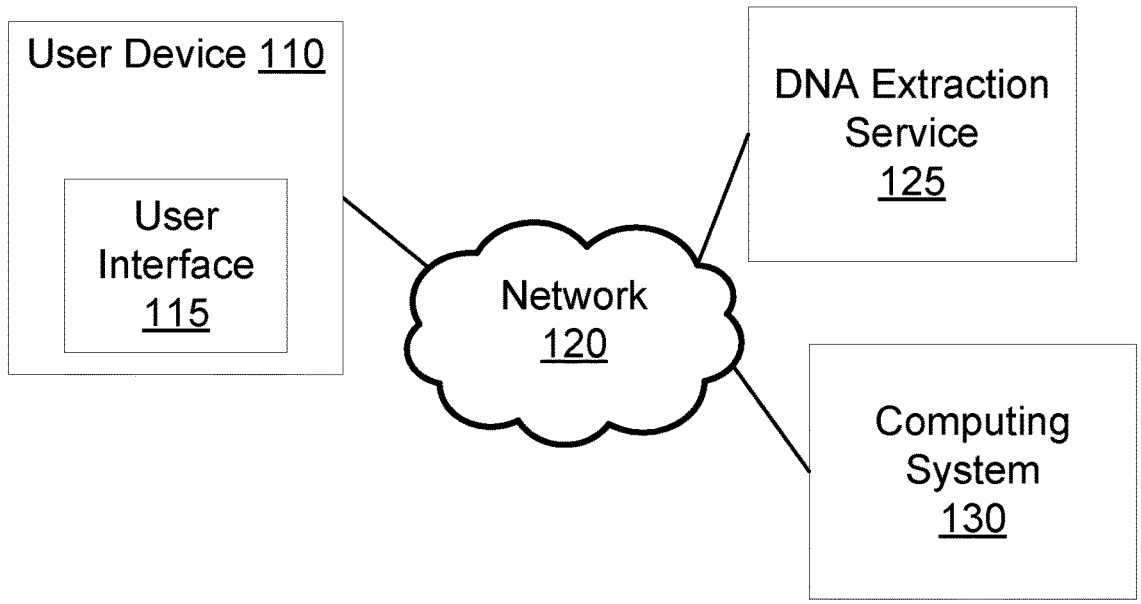
FIG. 1 illustrates a diagram of a system environment of a computing system, according to one embodiment.

FIG. 1 illustrates a diagram of a system environment 100 of a computing system 130, according to one embodiment. The system environment 100 shown in FIG. 1 includes a user device 110, a network 120, a deoxyribonucleic acid (DNA) extraction service 125, and a computing system 130. In alternative configurations, different, fewer and/or additional components may be included in the system environment 100.

The client devices 110 are one or more computing devices capable of receiving user input as well as transmitting and/or receiving data via a network 120. In one embodiment, a client device 110 is a computer system, such as a desktop or a laptop computer. Alternatively, a client device 110 may be a device having computer functionality, such as a personal digital assistant (PDA), a mobile telephone, a smartphone, or another suitable device. A client device 110 is configured to communicate via the network 120. In one embodiment, a client device 110 executes an application allowing a user of the client device 110 to interact with the computing system 130 via a user interface 115 of the client device. For example, a client device 110 executes a web browser application to enable interaction between the client device 110 and the computing system 130 via the network 120. In another embodiment, the user interface 115 takes the form of a graphical user interface as part of a software application published by the computer system 130 and installed on the user device 110. In yet another embodiment, a client device 110 interacts with the computing system 130 through an application programming interface (API) running on a native operating system of the client device 110, such as IOSC) or ANDROID™.

The client devices 110 are configured to communicate via a network 120, which may include any combination of local area and/or wide area networks, using both wired and/or wireless communication systems. In one embodiment, a network 120 uses standard communications technologies and/or protocols. For example, a network 120 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques.

Individuals provide DNA samples (or DNA datasets) for analysis of their genetic data. In one embodiment, an individual uses a sample collection kit to provide a DNA sample, e.g., saliva, from which genetic data can be reliably extracted according to DNA processing techniques such as DNA sequencing. DNA extraction service 125 receives the sample and estimates genotypes from the genetic data, for example by extracting the DNA from the sample and identifying genotype values of single nucleotide polymorphisms (SNPs) present within the DNA. The result in this example is a diploid genotype for each SNP site. The computing system 130 receives the genetic data from DNA extraction service 125 and stores the genetic data in a DNA sample store containing DNA diploid genotypes. In some embodiments, the genetic data stored in the DNA sample store may be associated with a user in the user data store via one or more pointers.

The computing system 130 processes the DNA to identify shared IBD between pairs of individuals, and uses that information to identify clusters in a sample of individuals. In one embodiment, a cluster includes individuals in a sample that exhibit a higher density of IBD connections between each other relative to other individuals in the sample. The clusters can be annotated with information about phenotypes characteristic and genealogical data of individuals within the group, and used to develop models that allow assignment of, often new, individuals to those clusters.

Figure 2:
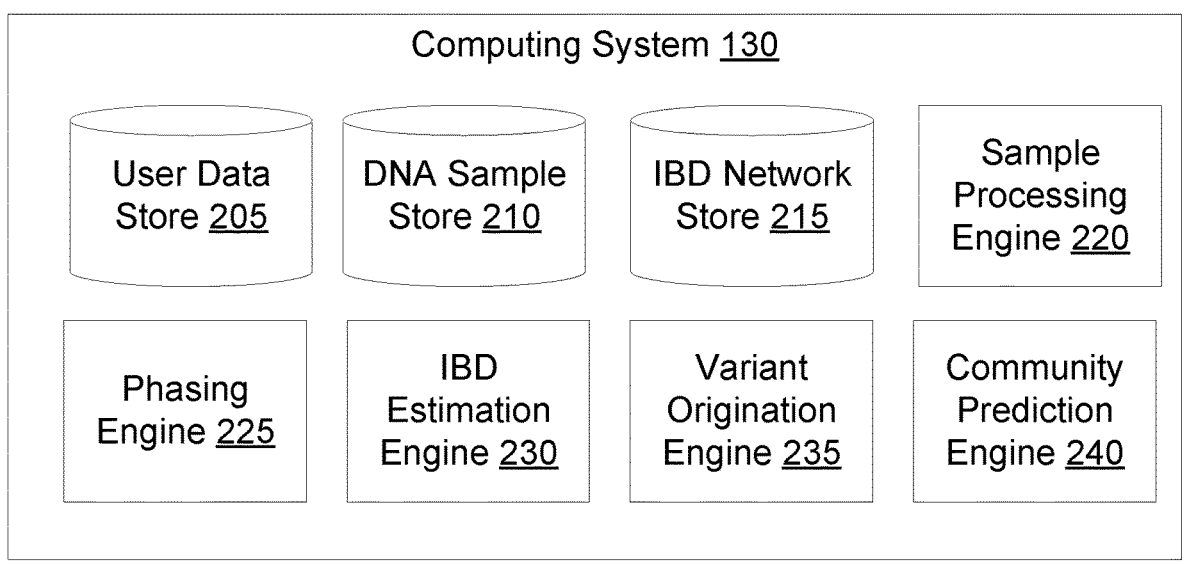
FIG. 2 is a block diagram of an architecture of the computing system, according to one embodiment.

FIG. 2 is a block diagram of an architecture of the computing system 130, according to one embodiment. In the embodiment shown in FIG. 2, the computing system 130 includes a user data store 205, a DNA sample store 210, a IBD network store 215, a sample processing engine 220, a phasing engine 225, a IBD estimation engine 230, a variant origination engine 235, and a community prediction engine 240. In addition, the functions may be distributed among the elements in a different manner than described. In various embodiments, the computing system 130 may include different, fewer, and/or additional components.

The computing system 130 maintains user data in the user data store 205. The store data store 205 maintains user data for each user of the computing system 130. The amount and type of data stored for each user in the user store 205 may vary based on the information provided by the corresponding user. Users may provide data via the user interface 115 of a user device 110. For example, the user may be prompted in an element of a user interface to answer questions related to the user that can be processed to obtain genealogical and survey data. Examples of genealogical data includes names (first, last, middle, suffixes), birth locations, date of birth, date of death, marriage information, kinships, family history, and the like. In some instances, family history can take the form of a pedigree of that individual (e.g., the recorded relationships in the family). The pedigree information associated with a user comprises one or more specified nodes. Each specified node in the pedigree represents either the individuals themselves or an ancestor of the individual corresponding to a stored DNA sample. Therefore, the nodes represent pedigree members that are either the individual themselves, or individuals that could have passed down genetic material to the associated individual. Genealogical data may also include genetic connections among users of the computing system 130. Examples of survey data include information about an individual's phenotypes, such as physical traits (e.g., height, hair, skin pigmentation, freckling, bitter taste, earlobe type, iris patterns, male pattern baldness, hair curl), wellness phenotypes (e.g., lactose tolerance, caffeine consumption, malaria resistance, norovirus resistance, muscle performance, alcohol flush), and personal preferences (e.g., likes and dislikes). The user data store 205 may also include information inferred from the DNA samples stored in the DNA store 210 and information received from the individuals. For example, information related to which individuals are genetically related, how they are related, how many generations back do they share common ancestors, percent IBD shared, which communities the individual is a part of, variants the individual carries, and the like.

The user data store 205 also includes genotypes of the individual generated from the DNA samples. Genotypes may be generated by the sample processing engine 220 or a third-party service. The user data store 205 may also include haplotypes of the individual. Haplotypes are generated by phasing the genotypes. In one embodiment, the user data store 205 contains information about known variants the corresponding individual is a carrier of (e.g., the type of variant, location of the variant, phenotypes associated with the variant). This information can be obtained from the computing system 130, a third-party database or obtained using a third-party software.

The computing system 130 maintains DNA samples of individuals in the DNA sample store 210. DNA samples may contain whole or portions of individual's DNA and corresponding metadata. The data stored in the DNA sample store 210 may store one or more DNA samples linked to a user. In various embodiments, the DNA sample store 210 stores a pointer to a location associated with the user data store 205 associated with the individual.

The sample processing engine 220 receives, processes, and stores data received from an individual via the user interface 115 of the user device 110 or the DNA extraction service 125. To collect the user data (e.g., genealogical and survey data), the sample processing engine may be configured to provide an interactive user interface on the user device 110 that provides interface elements in which users can provide genealogical data and survey data. These data may be manually provided or automatically extracted via, for example, optical character recognition (OCR) performed on census records, town or government records, or any other item of printed or online material.

To collect DNA samples, the sample processing engine 220 is configured to receive DNA samples via the DNA extraction service 125 or sample data from third party sources. The sample processing engine 220 may send the DNA samples to the DNA sample store 210 and to the phasing engine 225. The sample processing engine 220 identifies autosomal SNPs so that the individual's diploid genotype on autosomal chromosomes can be computationally phased. For example, for one individual 700,000 autosomal SNPs may be identified to estimate genotype phase. The sample processing engine 220 provides the identified SNPs to the phasing engine 225 which phases the individual's diploid genotype based on the set of identified SNPs to generate a set of haplotypes for each user.

The phasing engine 225 phases DNA samples so that an individual's haplotypes may be used by the IBD estimation engine 230, variant origination engine 235, and community prediction engine 240. The sets of haplotypes are used by the variant origination engine 235 to characterize variants of interest. The sets of haplotypes are also used by the community prediction engine 240 to determine an individual's membership in a community. The phasing engine 225 generates a pair of estimated haplotypes for each diploid genotype. The estimated haplotypes are stored in the user data store 205 and IBD network store 215. The phasing engine 225 stores phased genotypes in the user data store 205. For phasing a set of genotypes to generate two datasets of haplotype, U.S. patent application Ser. No. 15/591,099, entitled "Haplotype Phasing Models," filed Oct. 19, 2015 is incorporated by reference for all purposes.

The IBD estimation engine 230 estimates IBD segments from phased genotype data (haplotypes) between pairs of individuals stored in the user data store 205. IBD segments are chromosome segments identified in a pair of individuals that are putatively inherited from a recent common ancestor. Typically, individuals who are closely related share a relatively large number of IBD segments, and the IBD segments tend to have greater length (individually or in aggregate across one or more chromosomes), while individuals who are more distantly related share relatively few IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity.

IBD estimates are used to build IBD networks that identify individuals who share IBD genome wide and/or IBD at genetic loci. The variant origination engine 235 and the community prediction engine 240 use these networks to identify individuals who are carriers of particular variants and individuals who are a part of a genetic community.

In some embodiments, the IBD network may be used to construct data sets, referred to as reference panels, which can be used to train models. These models can in turn be used to generate a prediction regarding which clusters are relevant to a hypothetical user, such as a new user, based on a sample of their DNA. For example, a cluster may include individuals that are carriers of a particular variant, individuals who are a part of a community, individuals who share IBD at a genetic locus, etc. For more details on clustering and generation of reference panels, US Patent Publication No. US2016/0350479, entitled "Discovering Population Structure from Patterns of Identity-By-Descent," is hereby incorporated by reference for all purposes.

The variant origination engine 235 characterizes the origination of a variant. The characterization of a variant can provide insights into the origins, migration patterns, and historical and contemporary geographic distributions of populations carrying a variant of interest. Because variants are often associated with a trait, disease, or other phenotype, learning about a variant's origin and distribution may also contribute to the understanding of the etiology associated with the trait, disease, or other phenotype. To do this, the variant origination engine 235 performs an enrichment analysis on the genealogical data of users associated with a variant to identify enriched birth locations during distinct time periods. In some embodiments, users select a set of one or more target variants to characterize. Users may select target variants using interactive interface elements of a user interface 115 on a user device 110. Variant selection may be subject to criteria. Examples of criteria include allele frequency across populations, associated literature or known function, selection pressure, and autosomal or sex-linked inheritance.

The variant origination engine 235 may plot the results of the variant characterization on maps of various geographical locations. The graphical maps and plots described are useful because in various implementations they may be presented to a user via the user interface 115. However, actual generation of the graphical maps and plots is not strictly necessary in order to determine the geographic locations to annotate to a given variant. The description above may be accomplished entirely through non-graphical methods, that is by clustering data based on IBD affinity at the genetic loci of one or more variants of interest, accessing genealogical data of the cluster, and performing statistical analysis on the genealogical data of the cluster to determine the characterization of the variant without presenting results to users on a user interface. In some embodiments, the variant origination engine 235 generates a report of the variant characterization to users that have submitted genotypes and historical family records and have been identified as likely carriers of the variant. For example, the report may include the current and historical distributions, phenotypes associated with the variant, from which family members/ancestors the trait was inherited, years and locations of variant origination, and the like. The report may be presented on a user interface to the individuals in the cluster.

The community prediction engine 240 identifies which communities an individual belongs to using trained community-specific models. Therefore, the training process results in a collection of models that are configured to predict whether or not a given individual belongs to each community. For example, the community prediction engine 240 identifies that each user may be classified into zero, one or more communities. Model training and testing is discussed in detail below.

Once the models have been trained, the community prediction engine 240 can use the models to predict which, if any, communities a new user is a member of based on the new user's genetic sample. The system can use these community predictions to provide a report detailing the individual's predicted community membership without needing to re-build IBD networks or re-train models. In some embodiments, the report includes the binary classifications for the communities the user belongs to. In other embodiments, the report includes the portion of a user's DNA sample that belongs to each community. For example, a report may conclude that a user received 30% of their DNA from an Irish community and 70% of their DNA from a Finnish community. To do this, the amount of overlap between a user's haplotypes and a group of haplotypes representative of a community is used to determine the portion of DNA a user inherited from a particular community.

Figure 3A:
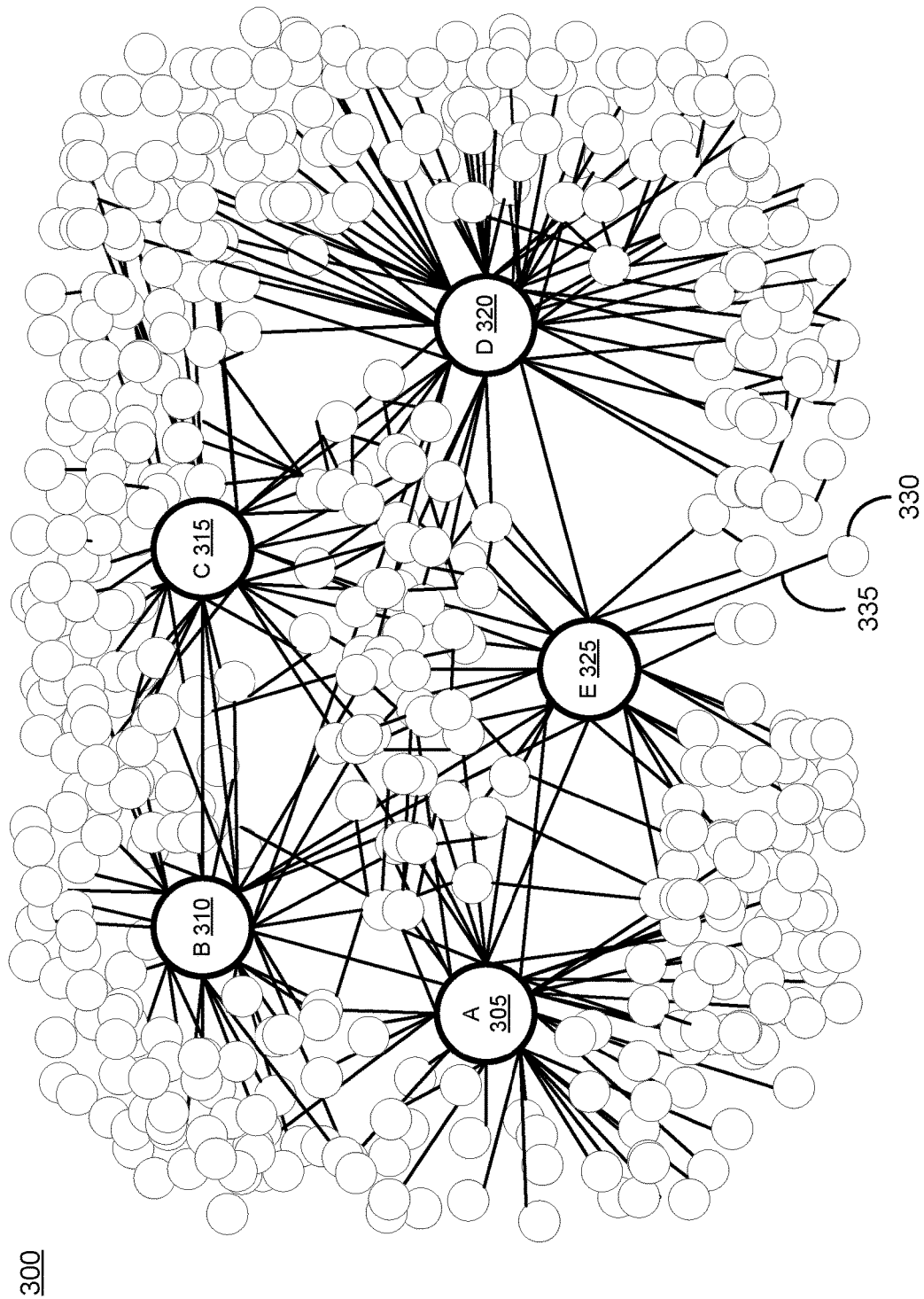
FIG. 3A illustrates an Identity-by-Descent (IBD) network that represents IBD sharing at genetic loci, according to one embodiment.

FIG. 3A illustrates an Identity-by-Descent (IBD) network 300 showing IBD sharing at genetic loci, according to one embodiment. An IBD network includes nodes, each corresponding to one of the individuals from the user data store 205. Each edge between one node and another node has a weight, a numerical value, based on the IBD estimate between the two nodes. For example, an edge may represent an IBD affinity between two nodes in an IBD network. More specifically, the IBD estimation engine 230 defines a mapping (also called an "affinity measure") from the total length of the shared IBD segments between two individuals (e.g., i and j) to the weight of the edge linking nodes i and j in the network. In one or more embodiments, the affinity measure is a real number between 0 and 1. For example, if the total length of the shared IBD segment between nodes i and j is greater than 65 cM (e.g., third cousins), then the edge linking nodes i and j receives a value of 0.97 or greater. Alternatively, if the total length of the shared IBD segment is 4-10 cM or less (e.g., distantly related or distant cousins), the edge may receive a weight of 0.

The IBD estimation engine 230 can partition the IBD network into two or more clusters using various algorithms. Clusters may be generated to identify individuals who share IBD at a genetic locus. For example, IBD sharing at the genetic locus of a variant of interest. Similarly, clusters may be generated to identify individuals who share haplotypes that are representative of a community. For example, IBD sharing at the genetic loci of a set of haplotypes that are only enriched in a particular community A cluster and community may be used interchangeably in some circumstances. Depending on the granularity, various clusters may represent different genetic communities, such as race and ethnicity groups, migration groups, local ancestors. For an IBD network, the computing system 130 may apply one or more clustering techniques such as K-means, Louvain clustering, etc. to generate one or more clusters of nodes. For example, in one embodiment, clusters in the IBD network are identified by selecting clusters that maximize the modularity objective defined with respect to the IBD network. Clusters identified from a network in this way are often referred to as "communities." Although modularity-maximizing algorithms may be employed to identify clusters in one or more embodiments, the term "community" is not used in the strict technical sense of a modularity-maximizing clustering, but is instead used more generally to refer to clusters identified in a network by taking any one of several existing network clustering approaches developed in the network analysis or machine learning areas.

Individuals in the network may share IBD genome wide or they may share IBD at a genetic locus. As shown in FIG. 3A, the IBD network 300 emphasizes individuals who share IBD with carriers of a variant of interest at the genetic locus of the variant of interest. Carriers, individuals who are affirmatively carriers of the variant, are represented as larger nodes. For example, nodes (circles) A 305, B 310, C 315, D 320, and E 325 represent carriers of the variant. The weights of the edges in the network may be computed to identify individuals who share IBD at the genetic locus of the variant of interest. Individuals who share IBD with carriers, but are not affirmatively carriers of the variant, are represented as smaller nodes in the network, e.g., individual 330. The nodes are connected to other nodes in the network via edges. For example, individual 330 is connect to carrier E 325 via edge 335.

Figure 3B:
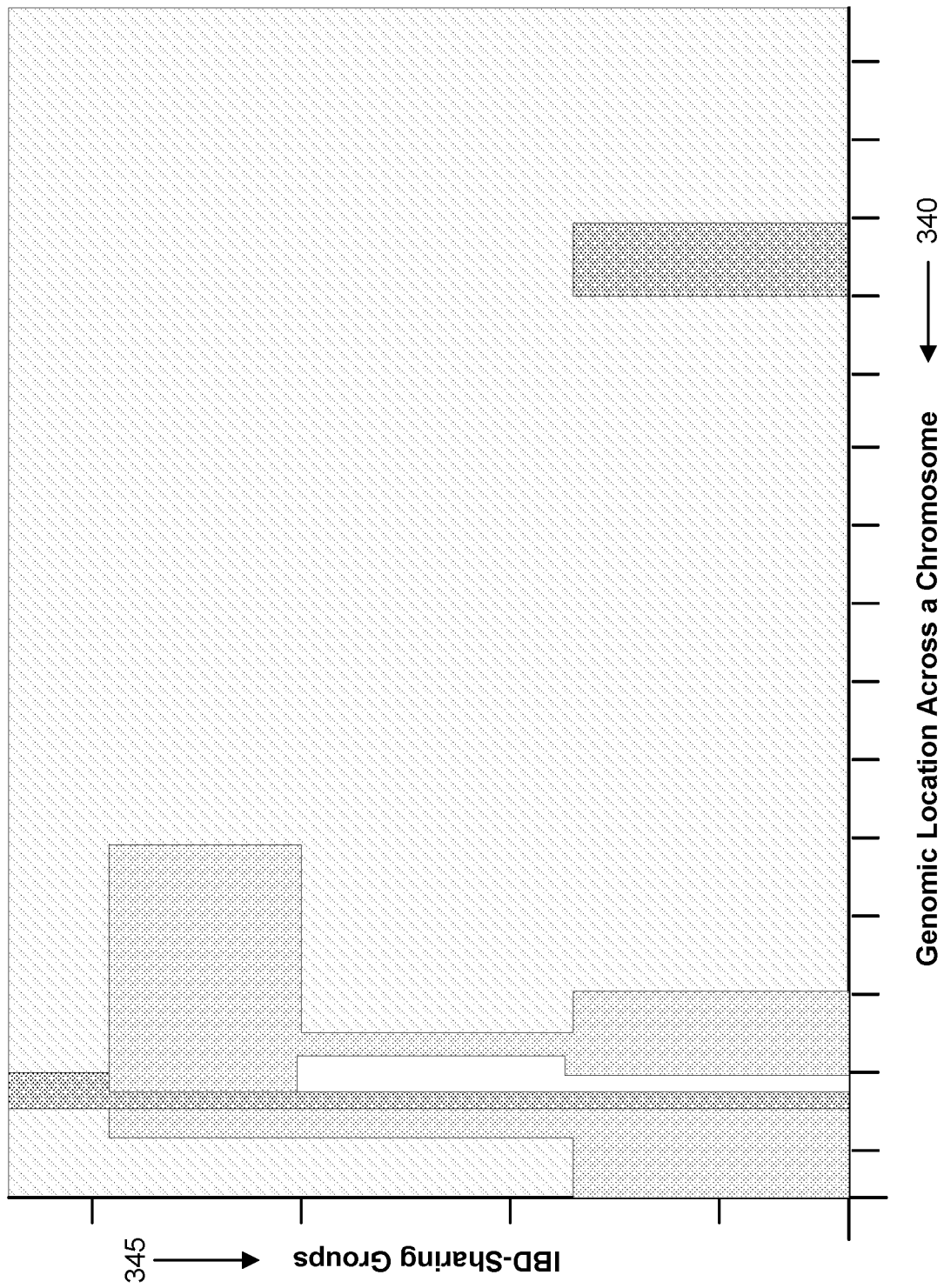
FIG. 3B illustrates IBD sharing at genetic loci across a chromosome, according to one embodiment.

FIG. 3B illustrates IBD sharing at genetic loci across a chromosome, according to one embodiment. Variants of interest may be detected by utilizing the degree of IBD between known samples (DNA samples of individuals who affirmatively carry the variant) and unknown samples (DNA samples of individuals who do not affirmatively carry the variant). For example, the computing system 130 can predict additional users that are probably carriers of the variant of interest based on an amount of IBD sharing between the known samples and unknown samples. In some embodiments, the unknown samples are compared to the known samples at the genetic locus of the variant of interest. In FIG. 3B, genomic locations across a chromosome 340 are represented along the x-axis. The y-axis indicates IBD-sharing groups 345, where each row is a sample's IBD relationship to samples of known carriers. The color or degree of shading indicates the number of samples that share IBD at the various locations along the chromosome. The lighter the color or shading, the more samples share IBD at that location. For example, the white region illustrates matches that are confirmed to have the variant, while the darker colored IBD sharing sample was confirmed to not have the variant. This illustrates the efficacy of detecting unknown variants in samples that have IBD to all of a subset of samples known to have the variant. Samples with IBD to just one or a few of the samples are expected to not have the variant of interest.

Figure 4:
FIG. 4 illustrates an example graphical representation of enriched birth locations, according to one embodiment.

FIG. 4 illustrates an example enriched birth location, according to one embodiment. To characterize a variant, the variant origination engine 235 performs an enrichment analysis to identify enriched birth locations within a cluster associated with a variant. Enriched birth locations are birth locations that are over-represented in a cluster during distinct periods of time. To generate the cluster, the variant origination engine 235 identifies individuals who are carriers of the variant ("reference individuals" or "carriers") and individuals who share IBD with the carriers. Carriers may be identified using information stored in the user data store 205, IBD network store 215, or information from a third-party service or software. In some embodiments, individuals are identified if they share IBD genome-wide with one or more carriers. For example, individuals are identified if they share a threshold amount of IBD genome-wide with one or more carriers. In other embodiments, individuals are identified only if they share IBD with one or more carriers at the genetic locus of the haplotype of the variant. Individuals who are IBD at the genetic locus of the haplotype of the variant are likely to also carry the variant. This is because if individuals have a long-shared segment of haplotypes, it is likely that they have all the same genetic information in that haplotype. Therefore, the variant origination engine 235 may use an IBD network of a region spanning a variant to identify and characterize individuals that may carry a target variant.

Individuals are added to the cluster based on the IBD affinity between the carriers and individuals that was calculated by the IBD estimation engine 230 using the genotypes of the individuals. For example, the genotypes of the e.g., genotypes 405A-D, were used to identify individuals 401A, 401B, 401C, and 401D as nodes of a cluster associated with a variant, e.g., Variant X. In some embodiments, individuals are added to the cluster if the IBD affinity between the corresponding individual and one or more carriers is above a threshold IBD affinity. By identifying additional users who share IBD with carriers, the variant origination engine 235 can characterize the origination of the variant with more statistical confidence than when only known carriers are used to characterize a variant. However, in some embodiments, variants may be characterized using only the data of users who are known carriers of the variant of interest.

The variant origination engine 230 extracts user data such as genealogical data associated with each node in the corresponding cluster (e.g., genealogical data 410A-D), as well as the node's relatives, such as ancestors. Examples of genealogical data may include family history, birth dates, birth locations, residences, dates of death, occupation, political and/or religious beliefs, marriages, and the like. Using this data, the variant origination engine 235 generates statistics to identify enriched birth locations. Statistics to identify enriched birth locations may include an odds ratio and frequency. The odds ratio is defined as the odds that, at a given location, an individual is a carrier of a variant over the odds that the individual is not a carrier of the variant.

The frequency is defined as the fraction of individuals born in a geographic location that carry a variant, trait, haplotype, genotype, etc. of interest (and/or share IBD with individuals that carry the variant of interest) and the total number of individuals born at the geographic location. An enriched birth location may be defined as a set of all rounded latitude-longitude grid points with an odds ratio of at least a threshold (e.g., 5) or with a log frequency of at least a threshold (e.g., 0.9), indicating a geographic location with a relative enrichment of birth locations. In other embodiments, different statistics may be used to identify enriched birth locations. Enrichment analysis may be repeated for different and distinct time periods to characterize the history of the variant. For example, the enrichment analysis for the cluster associated with Variant X identified Detroit, Michigan as an enriched birth location for the cluster during a distinct period of time (e.g., between 1930 A.D and 1960 A.D.). Additional enrichment analyses may be performed during different and additional periods of time to identify the historical distribution of the variant and/or migration patterns of Variant X. The results of the enrichment analysis and other genealogical data of the cluster are used to characterize the variant associated with the cluster. For example, migration patterns, current and historical distributions, average life span, variant origination, etc. associated with a variant may be identified. The characterization may be presented as a map, as discussed in FIG. 5, in a report, or in any other appropriate format. For more information regarding any enrichment analysis discussed in this disclosure, U.S. Patent Application Publication US 2017/0011042, entitled "Genetic and Genealogical Analysis for Identification of Birth Location and Surname Information" is incorporated by reference for all purposes.

In some embodiments, the variant origination engine 235 can assess the analytical validity of a variant from a founder population using IBD as evidence. If a variant is known to have arisen from a founder, the variant origination engine 235 can provide analytical validation of that variant by assessing whether the known carriers of the variant share IBD with each other at the genetic loci around and including the variant. Additionally, the variant origination engine 235 confirms that not all of the known carriers of the variant share IBD collectively with DNA samples that are not 'positive' for the variant (e.g., DNA samples of individuals known to not carry the variant).

As the IBD estimation engine 230 identifies additional users that share IBD at the genetic locus of a variant of interest, the variant origination engine 235 provides the characterization of the variant to the additional user. In some embodiments, the variant origination engine 235 adds the additional user to the cluster and reperforms the enrichment analysis using the additional user's DNA sample and genealogical data using various statistical tests (e.g., Fisher's exact test, chi-squared test, and the like). In some embodiments, similar analysis may be performed on phenotypes or haplotypes to characterize a phenotype or haplotype of interest.

Figure 5:
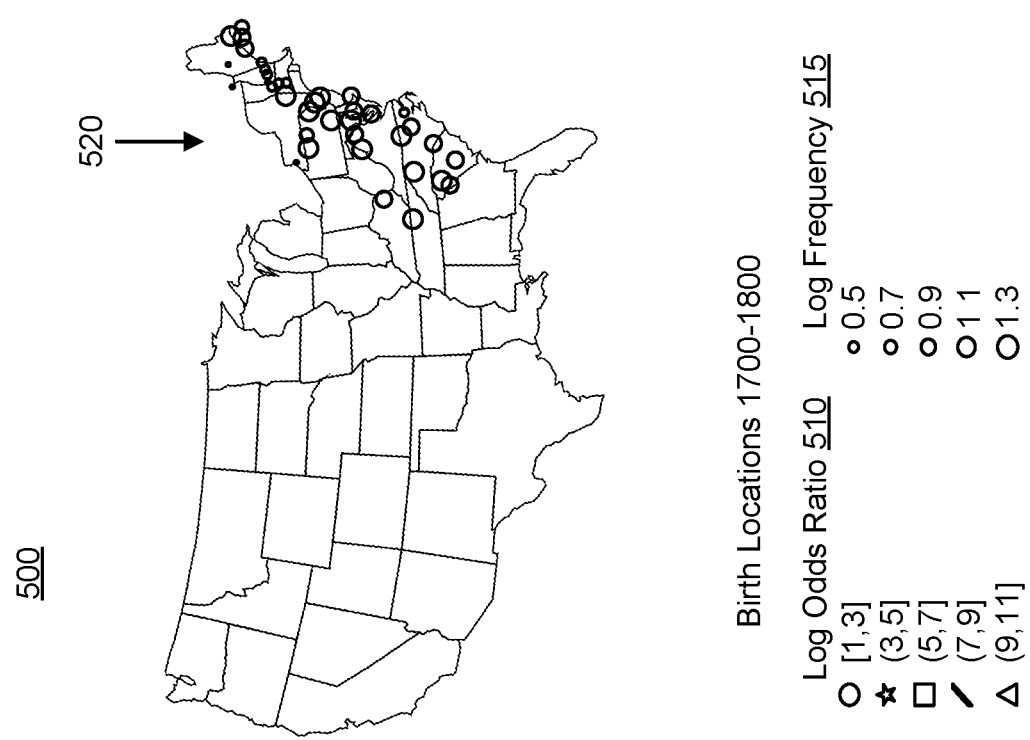
FIG. 5 illustrates example graphical representations of IBD-at-locus enriched birth locations plotted at various geographic locations, according to one embodiment.
Figure 5:
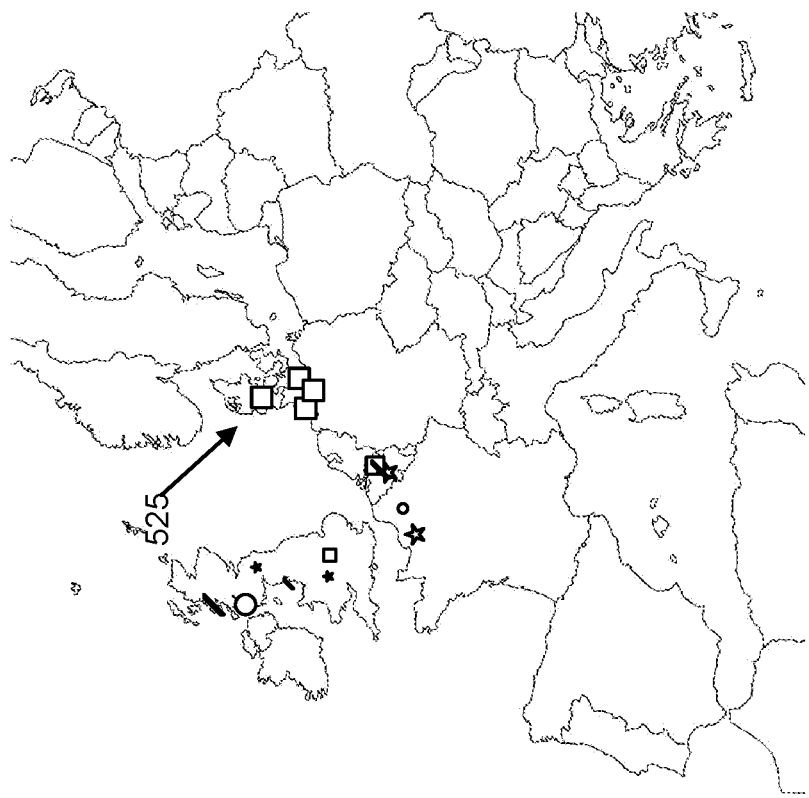

FIG. 5 illustrates example graphical representations of IBD-at-locus enriched birth locations plotted at various geographic locations, according to one embodiment. Maps may be used to visualize known geographic distributions of a common variant. Additionally, maps may be used to indicate possible origins and background populations for any chosen rare variant. In some embodiments, users select which geographic locations should be included in the map. In other embodiments, geographic locations are automatically included in the map based on the determined enriched locations. Similarly, in some embodiments, users may select which periods of time should be included in the map, and in other embodiments, periods of time are automatically included based on the characterization of the variant.

The illustration 500 shown depicts the birth locations of individuals who were born between the years 1700 A.D. and 1800 A.D, were carriers of a variant, trait, phenotype, haplotype, etc. of interest, and were born in the United States or Europe. It is shown in FIG. 5 that the variant is widespread throughout Northern Europe and the east coast of the United States. Additionally, the East Coast may have acted as a United States entry point for the variant. Users may also select different or additional variants to characterize using a user interface. To characterize different or additional variants, statistical filters can be adjusted on the amount of IBD sharing required to belong to a population or cluster.

Adjusted statistical filters are applied to individuals in the cluster to produce an updated cluster. Alternatively, a new cluster may be generated based on the genetic loci of the different and/or additional variants of interest.

Examples of statistics that are computed during the enrichment analysis include odds ratio and frequency. The odds ratio is defined as the odds that, at a given location, an individual is a carrier of a variant over the odds that the individual is not a carrier of the variant. The log of the odds ratio 510 is used to generate a graph that visually depicts grid points in which the largest log odds ratios are indicated visually by labels or distinguishable shapes. For example, a circle indicates the log of the odds ratio is between 1 and 3; a star indicates the log of the odds ratio is between 3 and 5; a square indicates the log of the odds ratio is between 5 and 7, etc. In this way, the highlighted graphical map locations correspond to birth locations that are disproportionately represented by carriers of the variant of interest. For example, individuals born in Denmark 525 between 1700 A.D. and 1800 A.D. are likely to be carriers of a variant, e.g., Variant X.

The frequency is defined as the fraction of individuals born in a geographic location that carry a variant, trait, haplotype, genotype, etc. of interest (and/or share IBD with individuals that carry the variant of interest) and the total number of individuals born at the geographic location. Frequency can be calculated for distinct time periods to identify the origin, migration patterns, and historical and contemporary distributions of a variant, trait, haplotype, or genotype of interest. The log frequency 515 is used to generate a graph that visually depicts grid points in which the greatest frequency ratios are indicated visually by labels or the size of the marker. The size of the marker indicates a log frequency 515 of the variant in a particular location. As shown, the larger the circle, the more frequently individuals born in a particular location are carriers of the variant. For example, as shown in the illustration 500, on the east coast of the United States 520, individuals born on the East Coast were frequently carriers of Variant X or shared IBD with carriers of Variant X.

Figure 6:
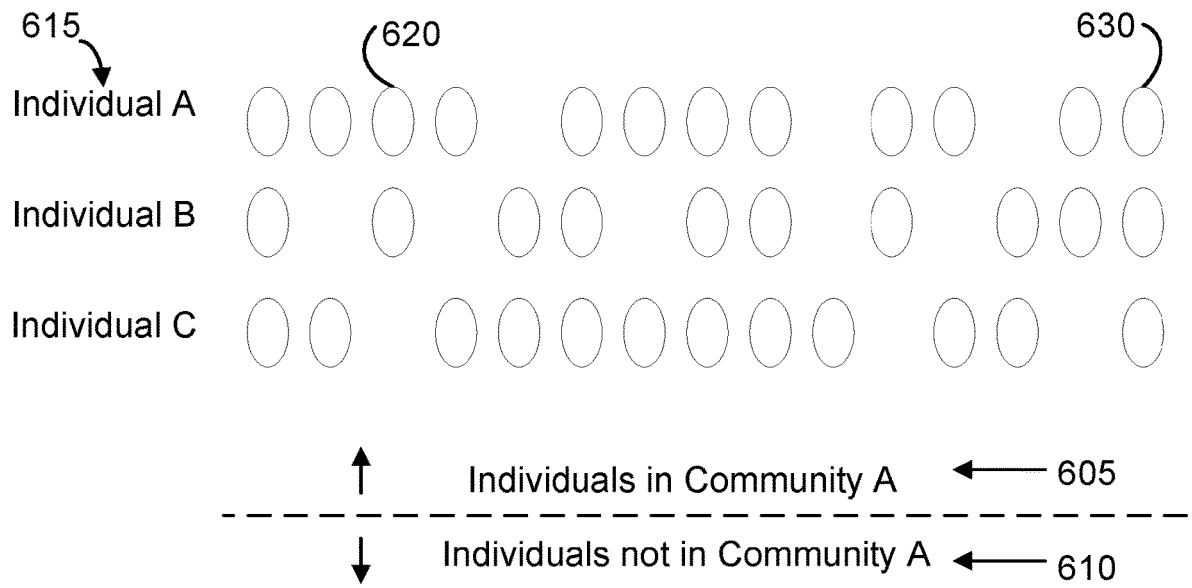
FIG. 6 illustrates a visual distinction in DNA data between individuals inside and outside a community using their haplotypes, according to one embodiment.
Figure 6:
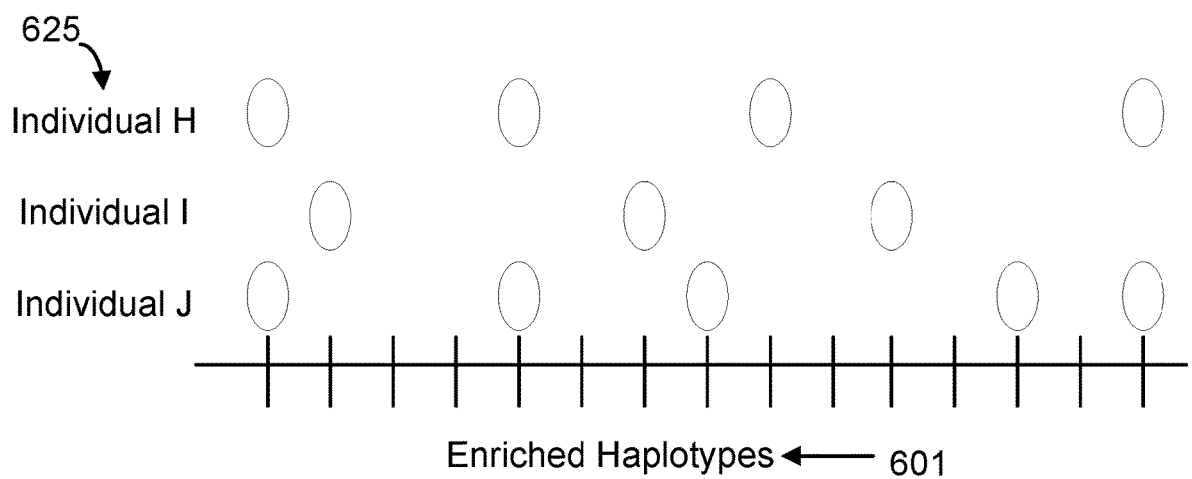

FIG. 6 illustrates the visual distinction of DNA datasets between individuals inside and outside a community using their haplotypes 600, according to one embodiment. These distinctions are used to predict whether or not an individual belongs to a community. To do this, the haplotypes of the user are inputted into one or more of the community-specific models as a feature vector. Each model will receive a different feature vector depending on which features (i.e., enriched haplotypes) were selected and used to train the community-specific model, discussed below. Enriched haplotypes are haplotypes that are uniquely common among members of a community. Thus, the estimated IBD that is relevant to the community classification will be different for each model (and hence, for each community). In one embodiment, each model computes a score, such as a binary score, a probability, or a likelihood, such as a p-value, to determine whether the input feature vector belongs to the community. In one implementation, an individual is classified as belonging a given community if the probability computed by the trained model exceeds a threshold numerical value. In some embodiments, the community prediction engine 240 sets the threshold numerical value. In other embodiments, users may select the threshold numerical value. The threshold for classifying individuals to communities may be the same or different for each model. The output of the community prediction module includes both a binary classification that an individual belongs to a community and the probability for each community. In some embodiments, the output includes the portion of an individual's DNA sample that belongs to each community. For example, the amount of overlap between a user's haplotypes and a group of haplotypes representative of a community may be used to determine the portion of DNA an individual inherited from a particular community.

In FIG. 6, each row represents an individual and each column represents a uniquely common haplotype within a community of interest (e.g., enriched haplotypes). Enriched haplotypes 601 are identified using the enrichment analysis described below. To more easily visualize the distinction between the haplotypes of individuals who do or do not belong to a community, individuals 605 whose haplotypes are shown above the dotted line belong to Community A, and individuals 610 whose haplotypes are shown below the dotted line do not belong to Community A. The enriched haplotypes 601 do not represent the haplotypes of a single individual. Rather, they represent a set of haplotypes that are most representative of the community and can be used as features in a model and/or classifier. Therefore, individuals do not need to have all of the haplotypes in the set of haplotypes, nor do individuals need to have the all the same haplotypes of other individuals to be a part of the same community.

Individuals are identified as belonging to a community based on the number of enriched haplotypes of a community they have. The more enriched haplotypes of a community they carry, the greater the likelihood they belong to that community. As shown, individuals that have at least a threshold number of enriched haplotypes of Community A are members of Community A. Similarly, individuals that carry less than a threshold number of enriched haplotypes of Community A are not members of Community A. For example, Individual A 615 is a carrier of 12 of the 15 enriched haplotypes of Community A, e.g., haplotype 620 and haplotype 630, and Individual H 625 is only a carrier of 4 of the 15 enriched haplotypes of Community A.

Models are trained using training and testing datasets sets created for each community. Training and testing datasets are generated by phasing the genotypes of individuals who belong to a community of interest and individuals who do not belong to the community of interest. Training of the models may be supervised. For example, each individual in the training and testing datasets may have a binary label indicating whether or not they belong to the community. If an individual is known to belong to a community, the individual is labeled with a "1". Similarly, if an individual is known to not belong to the community, the individual is labeled with a "0". Positive training sets comprise groups of haplotypes of individuals known to belong to a community. Negative training sets comprise groups of haplotypes of individuals known to not belong to a community.

The genotypes of the community members are analyzed to find the common haplotypes at each window. For example, common haplotypes are of window lengths of 64, 128, and 512 SNPs). An enrichment analysis is performed on the common haplotypes to find which common haplotypes are more likely to be observed in the community of interest compared to other communities ("enriched haplotypes") 601. In one embodiment, Fisher's exact tests are used during the enrichment analysis to identify enriched haplotypes. In another embodiment, chi-square tests are used to identify enriched haplotypes. Bonferroni corrections may be used to avoid false positives. Enriched haplotypes, also referred to as reference haplotypes, are used as features in a community-specific model. Models may be linear or non-linear, and may include random forest classifiers, SVMs, neural networks, decision trees. A feature vector is generated for each individual in the training and testing datasets. Each element in the feature vector corresponds to a reference haplotype, and the value of each element indicates the presence or absence of the reference haplotype in the individual. For example, if an individual has a feature, the corresponding element in the feature vector has a value of "1", and if the individual does not have a feature, the corresponding element in the feature vector has a value of "0".

The community prediction engine 240 generates a data frame that includes the individuals with their feature vector and the label indicating whether or not they belong in the community. The model is applied to the data frame, and the performance of the model is measured. The analysis of the model may be performed multiple times based on a chosen length of haplotypes (e.g., 64, 128, 512 SNPs). In some embodiments, haplotypes of different lengths are mixed during analysis. In other embodiments, haplotypes of a single length are used during analysis. Final model parameters and weights are chosen based on model performance.

Figure 7:
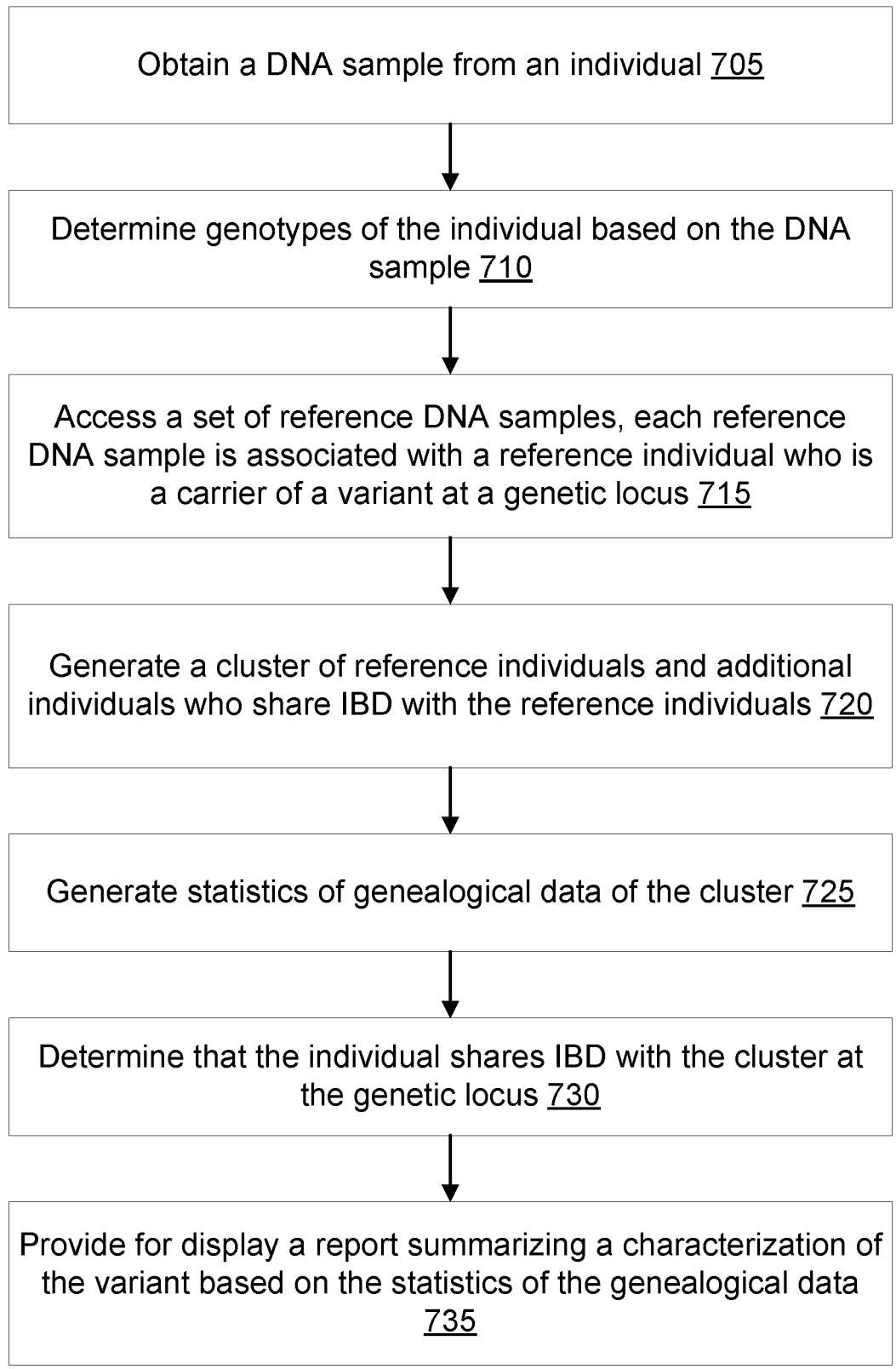
FIG. 7 is a flow chart illustrating a method of characterizing a variant, according to one embodiment.

FIG. 7 is a flow chart illustrating a method 700 of characterizing a variant, according to one embodiment. A DNA sample for an individual is obtained 705. The genotypes of the individual are determined 710 based on the DNA sample. A set of reference DNA samples are accessed 715. Each reference DNA sample is associated with a reference individual who is a carrier of an allele (or variant) at a genetic locus. A cluster that includes the reference individuals and additional individuals is generated 720. The cluster may be generated 720 based on IBD affinity between the reference individuals and the additional individuals. The additional individuals may share IBD genome-wide with the reference individuals or IBD at the genetic locus of the variant. Genealogical data of the individuals in the cluster is obtained. For example, the birth location and birth year of each individual in the cluster and the ancestors of each individual. Statistics of the genealogical data of the cluster are generated 725. For example, the odds ratio and frequency of the variant are generated 725 to identify enriched birth locations of the cluster. Once it is determined 730 that the individual shares IBD with the cluster at the genetic locus, a report summarizing a characterization of the variant based on the statistics of the genealogical data is provided 735 for display. In other embodiments, users may access characterizations of variant, traits, phenotypes, haplotypes, etc., without sharing IBD with individuals who are carriers.

Figure 8:
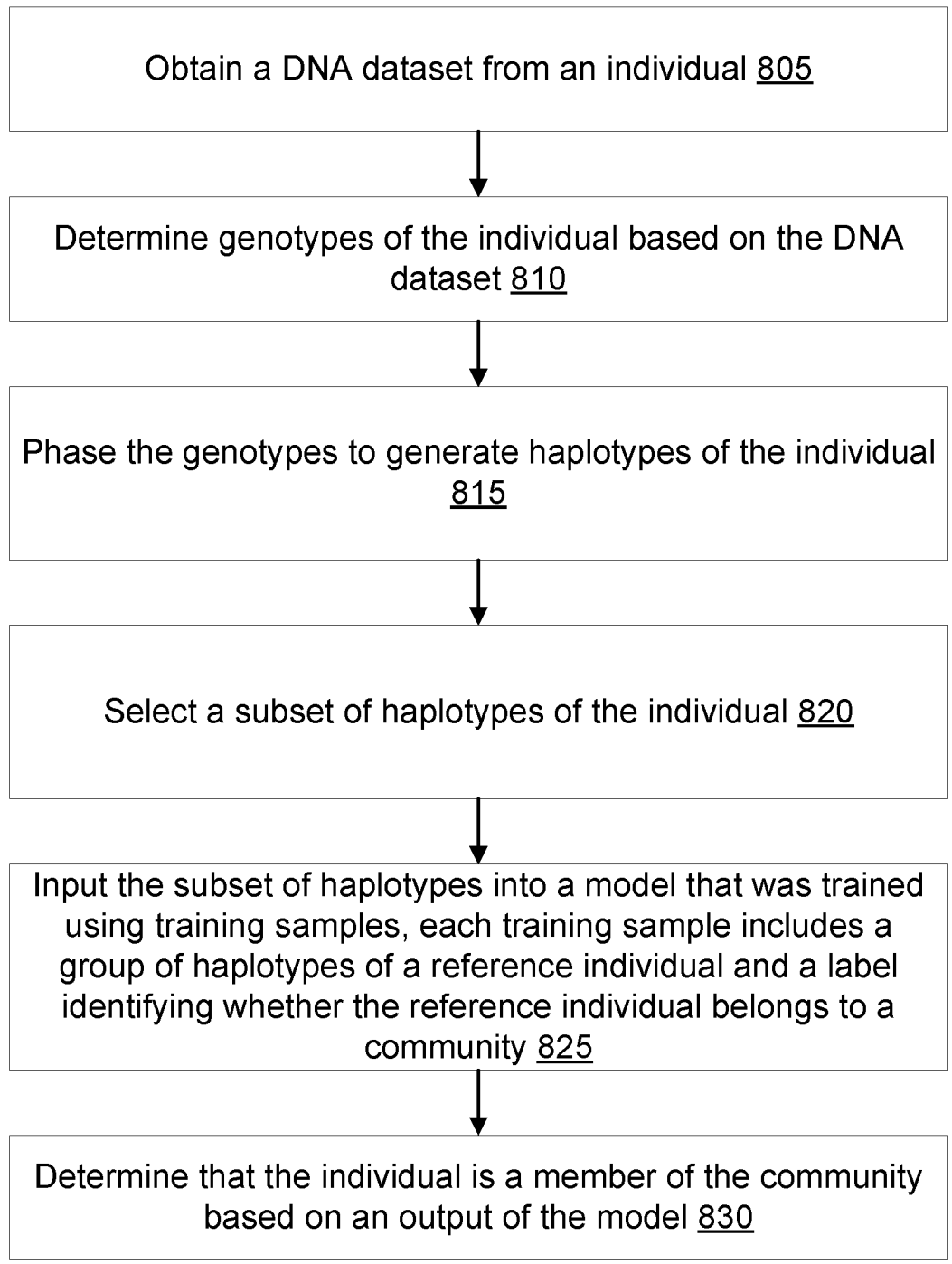
FIG. 8 is a flow chart illustrating a method of using a model to predict if an individual is a member of a community, according to one embodiment.

FIG. 8 is a flow chart illustrating a method 800 of using a model to predict if an individual is a member of a community, according to one embodiment. A DNA dataset is obtained 805 from an individual. The genotypes of the individual are determined 810 based on the DNA dataset. The genotypes of the individual are phased 815 to generate haplotypes of the individual. A subset of haplotypes of the individual are selected 820. For example, a subset of haplotypes is selected based on a community of interest. A different subset of haplotypes may be selected for each community of interest. The subset of haplotypes is inputted 825 into a model that was trained using training samples. Each training sample includes a group of haplotypes of a reference individual and a label identifying whether the reference individual belong to a community. Based on the output of the model, it is determined 830 whether the individual is a member of the community. To determine if an individual is a member of additional communities, different subsets of haplotypes are inputted into different community-specific models. For example, there are models to determine if an individual belong to an Irish community, a Jewish community, or a Finnish community.

FIG. 9 is a flow chart illustrating an additional method 900 of characterizing a variant, according to one embodiment. A request to generate a report of a target set of one or more variants of a user of a computing system is received 905. A group of one or more carriers that are known to be carrying the one or more variants specified in the target set is identified 910. DNA datasets of the carriers are accessed 915. DNA datasets of additional individuals who share Identity-by-Descent (IBD) with at least one of the carriers at a genetic locus that includes the one or more variants specified in the target set are accessed 920. Genealogical data of the carriers and the additional individuals is accessed 925. A result summarizing a characterization of the one or more variants based on an association between the one or more variants and the genealogical data of the carriers and the additional individuals is generated 930.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

What is claimed is:

1. A method comprising:
   obtaining a DNA dataset from an individual;
   determining genotypes of the individual based on the DNA dataset;
   phasing the genotypes to generate haplotypes of the individual;
   retrieving a plurality of community-specific random forest machine learning models, each community-specific random forest machine learning model is specific to a community, each community-specific random forest machine learning model is trained by enriched haplotype features of reference individuals and labels identifying whether the reference individuals belong to the community, a reference individual who belongs to the community having the enriched haplotype features that are representative of the community;
   extracting sets of community-specific features from the haplotypes of the individuals, wherein each set comprises corresponding enriched haplotype features of the individual specific to the community;
   inputting, for each community-specific random forest machine learning model, the set of community-specific features into the community-specific random forest machine learning model, to generate a community-specific score; and
   determining whether the individual is a member of a particular community based on community-specific scores generated by the plurality of community-specific random forest machine learning models.

2. The method of claim 1, wherein one of the community-specific random forest machine learning models is further trained by at least:
   phasing genotypes of reference individuals;
   identifying common haplotypes at each window of the genotypes;
   performing an enrichment analysis on the common haplotypes to identify a set of enriched haplotypes;
   generating a feature vector for each reference individual, the feature vector has a set of binary elements, each associated with an enriched haplotype, a value of each binary element indicating whether the reference individual has the enriched haplotype;
   generating a data frame that includes the reference individuals with their feature vector and the label identifying whether the reference individual belongs to the community;
   applying the community-specific random forest machine learning model to the data frame, the enriched haplotypes are features of the model; and
   adjusting parameters of the community-specific random forest machine learning model based on a performance of the community-specific random forest machine learning model.

3. The method of claim 1, wherein each community-specific random forest machine learning model is trained by training samples, and a positive training sample of the training samples is generated by at least:
   phasing a DNA dataset of one of the reference individuals who belongs to the community to generate haplotypes of the reference individuals;
   performing an enrichment analysis on the haplotypes with respect to the community;
   identifying one or more groups of haplotypes of the reference individual that are representative of the community;
   extracting the one or more groups of haplotypes as the positive training sample; and
   associating the positive training sample with a positive label that the reference individual belongs to the community.

4. The method of claim 3, wherein a negative training sample of the training samples is generated by at least:
   retrieving a DNA dataset of a reference individual who is known not belonging to the community;
   extracting one or more groups of haplotypes as the negative training sample, the extracted one or more groups of haplotypes being at same genetic loci of the one or more groups of haplotypes of the one of the reference individuals who belongs to the community; and
   associating the negative training sample with a negative label that the reference individual does not belong to the community.

5. The method of claim 1, wherein the enriched haplotype features are identified using an enrichment analysis to determine which haplotypes are more likely to be observed in a community.

6. The method of claim 1, wherein one of the community-specific random forest machine learning models is a non-linear classifier selected from a group consisting of a support vector machine, one or more decision trees, or a neural network.

7. A computer-readable storage medium having stored thereon computer-executable instructions that, when executed by one or more processors, causes the one or more processors to perform at least the following:
   obtain a DNA dataset from an individual;
   determine genotypes of the individual based on the DNA dataset;
   phase the genotypes to generate haplotypes of the individual;
   retrieve a plurality of community-specific random forest machine learning models, each community-specific random forest machine learning model is specific to a community, each community-specific random forest machine learning model is trained by enriched haplotype features of reference individuals and labels identifying whether the reference individuals belong to the community, a reference individual who belongs to the community having the enriched haplotype features that are representative of the community;
   extract sets of community-specific features from the haplotypes of the individuals, wherein each set comprises corresponding enriched haplotype features of the individual specific to the community;
   input, for each community-specific random forest machine learning model, the set of community-specific features into the community-specific random forest machine learning model, to generate a community-specific score; and determine whether the individual is a member of a particular community based on community-specific scores generated by the plurality of community-specific random forest machine learning models.

8. The computer-readable storage medium of claim 7, wherein one of the community-specific random forest machine learning models is further trained by at least:
   phasing genotypes of reference individuals;
   identifying common haplotypes at each window of the genotypes;
   performing an enrichment analysis on the common haplotypes to identify a set of enriched haplotypes;
   generating a feature vector for each reference individual, the feature vector has a set of binary elements, each associated with an enriched haplotype, a value of each binary element indicating whether the reference individual has the enriched haplotype;
   generating a data frame that includes the reference individuals with their feature vector and the label identifying whether the reference individual belongs to the community;
   applying the community-specific random forest machine learning model to the data frame, the enriched haplotypes are features of the model; and
   adjusting parameters of the community-specific random forest machine learning model based on a performance of the community-specific random forest machine learning model.

9. The computer-readable storage medium of claim 7, wherein each community-specific random forest machine learning model is trained by training samples, and a positive training sample of the training samples is generated by at least:
   phasing a DNA dataset of one of the reference individuals who belongs to the community to generate haplotypes of the reference individuals;
   performing an enrichment analysis on the haplotypes with respect to the community;
   identifying one or more groups of haplotypes of the reference individual that are representative of the community;
   extracting the one or more groups of haplotypes as the positive training sample; and
   associating the positive training sample with a positive label that the reference individual belongs to the community.

10. The computer-readable storage medium of claim 9, wherein a negative training sample of the training samples is generated by at least:
    retrieving a DNA dataset of a reference individual who is known not belonging to the community;
    extracting one or more groups of haplotypes as the negative training sample, the extracted one or more groups of haplotypes being at same genetic loci of the one or more groups of haplotypes of the one of the reference individuals who belongs to the community; and
    associating the negative training sample with a negative label that the reference individual does not belong to the community.

11. The computer-readable storage medium of claim 7, wherein
    the enriched haplotype features are identified using an enrichment analysis to determine which haplotypes are more likely to be observed in a community.

12. The computer-readable storage medium of claim 7, wherein one of the community-specific random forest machine learning models is a non-linear classifier selected from a group consisting of a support vector machine, one or more decision trees, or a neural network.

13. A computer system for determining whether an individual is a member of a target genetic community, the computer system comprising:
    one or more processors;
    a hardware storage device having stored thereon computer-executable instructions that, when executed by the one or more processors, causes the computer system to perform at least the following:
      determine genotypes of an individual based on an associated DNA dataset for the individual;
      phase the determined genotypes to generate a set of haplotypes of the individual;
      retrieve a plurality of community-specific random forest machine learning models, each community-specific random forest machine learning model is specific to a community, each community-specific random forest machine learning model is trained by enriched haplotype features of reference individuals and labels identifying whether the reference individuals belong to the community, a reference individual who belongs to the community having the enriched haplotype features that are representative of the community;
      extract sets of community-specific features from the haplotypes of the individuals, wherein each set comprises corresponding enriched haplotype features of the individual specific to the community;
      input, for each community-specific random forest machine learning model, the set of community-specific features into the community-specific random forest machine learning model, to generate a community-specific score; and
    determine whether the individual is a member of a particular community based on community-specific scores generated by the plurality of community-specific random forest machine learning models.

14. The computer system of claim 13, wherein the output of the one of the community-specific random forest machine learning models comprises a numerical probability that the individual is a member of the target genetic community.

15. The computer system of claim 14, wherein the individual is determined to be a member of the particular community if the numerical probability exceeds a threshold numerical value.

16. The computer system of claim 15, wherein the output of the one of the community-specific random forest machine learning models further comprises a binary classification that the individual is a member of the target genetic community, the binary classification based on whether the numerical probability exceeds the threshold numerical value.

17. The computer system of claim 13, wherein one of the community-specific random forest machine learning models is a non-linear classifier selected from the group consisting of a support vector machine, one or more decision trees, and a neural network.

18. The computer system of claim 13, wherein the enriched haplotype features comprise haplotypes having differing window lengths of single nucleotide polymorphisms.

19. The computer system of claim 13, wherein the enriched haplotype features comprise haplotypes having a window length of at least 64 single nucleotide polymorphisms.

20. The computer system of claim 13, wherein one of the community-specific random forest machine learning models is further trained by at least:
    phasing genotypes of reference individuals;
    identifying common haplotypes at each window of the genotypes;
    performing an enrichment analysis on the common haplotypes to identify a set of enriched haplotypes;
    generating a feature vector for each reference individual, the feature vector has a set of binary elements, each associated with an enriched haplotype, a value of each binary element indicating whether the reference individual has the enriched haplotype;
    generating a data frame that includes the reference individuals with their feature vector and the label identifying whether the reference individual belongs to the community;
    applying the community-specific random forest machine learning model to the data frame, the enriched haplotypes are features of the model; and
    adjusting parameters of the community-specific random forest machine learning model based on a performance of the community-specific random forest machine learning model.

\* \* \* \* \*